(12) United States Patent
Bengtsson et al.

(10) Patent No.: US 7,569,736 B2
(45) Date of Patent: Aug. 4, 2009

(54) PROCESS FOR PRODUCING MONOPENTAERYTHRITOL OF HIGH PURITY AND MONOPENTAERYTHRITOL PRODUCED BY THE PROCESS

(75) Inventors: Hans-Ake Bengtsson, Bjarnum (SE); Lars-Henrik Nyman, Hassleholm (SE)

(73) Assignee: Perstorp Specialty Chemicals AB, Perstorp (SE)

( * ) Notice: Subject to any disclaimer, the term of this patent is extended or adjusted under 35 U.S.C. 154(b) by 0 days.

(21) Appl. No.: 12/162,423

(22) PCT Filed: Feb. 5, 2007

(86) PCT No.: PCT/SE2007/000100

§ 371 (c)(1),
(2), (4) Date: Oct. 17, 2008

(87) PCT Pub. No.: WO2007/089197

PCT Pub. Date: Aug. 9, 2007

(65) Prior Publication Data

US 2009/0062575 A1     Mar. 5, 2009

(30) Foreign Application Priority Data

Feb. 3, 2006   (SE) .................................. 0600228

(51) Int. Cl.
*C07C 31/24* (2006.01)
*C07C 29/38* (2006.01)

(52) U.S. Cl. ...................................... 568/853; 568/854
(58) Field of Classification Search ................ 568/853, 568/854
See application file for complete search history.

(56) References Cited

FOREIGN PATENT DOCUMENTS

| RU | 2053215 | 1/1996 |
|----|---------|--------|
| RU | 2199518 | 2/2003 |
| SU | 1728215 | 4/1992 |

*Primary Examiner*—Elvis O Price
(74) *Attorney, Agent, or Firm*—Oblon, Spivak, McClelland, Maier & Neustadt, P.C.

(57) ABSTRACT

The invention relates to a process for producing monopentaerythritol of high purity and monopentaerythritol produced by the process. Formaldehyde is reacted with acetaldehyde in an aqueous solution in the presence of a strongly basic hydroxide in a conventional way. The obtained reaction mixture is evaporated to a dryness of 50-70% by weight and is thereafter cooled. Crystals of pentaerythritol thereby formed are separated off. The crystals are dissolved in water or in a water-containing mother liquor containing pentaerythritol to a dryness of 35-55% by weight. The solution is treated in a purification step whereupon monopentaerythritol of high purity is crystallized at a temperature of 40-90° C. and separated from the remaining mother liquor which is recirculated to the above mentioned step.

12 Claims, No Drawings

PROCESS FOR PRODUCING MONOPENTAERYTHRITOL OF HIGH PURITY AND MONOPENTAERYTHRITOL PRODUCED BY THE PROCESS

The present invention relates to a process for producing monopentaerythritol of high purity and monopentaerythritol produced by the process.

It has for a long time been known that pentaerythritol can be synthesised by a reaction between 4 moles of formaldehyde and 1 mole of acetaldehyde, where the reaction is carried out in an alkaline solution. It is assumed that 1 mole of acetaldehyde first reacts with 3 moles of formaldehyde to form pentaerythritose, which compound then reacts with additionally 1 mole of formaldehyde and alkali to form 1 mole of pentaerythritol and 1 mole of formate. The above mentioned reactions can be illustrated by the formulas below, where $Me^+$ can be for example $Na^+$ or $K^+$.

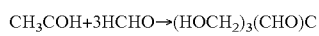

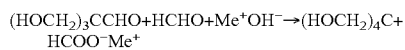

It is generally known that the yield of pentaerythritol obtained is slightly better calculated on acetaldehyde when using a surplus of formaldehyde and that at the same time the amount of monopentaerythritol increases at the expense of the amount of dipentaerythritol and higher pentaerythritol homologues.

In the above reaction not only monopentaerythritol is obtained but also to a certain degree both di- and tripentaerythritol as well as formate. In certain applications great advantages are obtained by using monopentaerythritol of high purity. Therefore, for a long time there has been a strong desire to be able to produce monopentaerythritol in pure form in a more economically advantageous and reliable way. Previously this has not been possible since dipentaerythritol and tripentaerythritol easily crystallize together with monopentaerythritol.

According to the present invention the above mentioned desire now has quite unexpectedly been fulfilled and a process for producing monopentaerythritol of high purity has been brought about wherein formaldehyde is reacted with acetaldehyde in an aqueous solution in the presence of a strongly basic hydroxide, preferably an alkali metal hydroxide or an alkaline earth metal hydroxide, at a molar ratio formaldehyde:acetaldehyde of 5-10:1, preferably 6-9:1, whereupon the reaction mixture is neutralized. The invention is characterized in that the reaction mixture obtained is evaporated to a dryness of 50-70% by weight and thereafter cooled. Crystals of pentaerythritol thereby formed are separated off, preferably by means of a band filter or a centrifuge, and dissolved in a water-containing mother liquor containing pentaerythritol to a dryness of 35-55% by weight. The solution is treated in a purification step whereupon monopentaerythritol of high purity is crystallized at a temperature of 40-90° C., preferably 45-80° C., and separated off from the remaining mother liquor that is processed and later recirculated to the above mentioned step.

The synthesis according to the invention can be carried out in a conventional way. Sodium hydroxide is appropriate to use but also potassium hydroxide is a possible alternative. The reaction is exothermic. The temperature rises during the synthesis. The end temperature is between 40-70° C. Possibly, cooling can be applied to regulate the temperature.

According to the invention a purification step is suitably used comprising coal treatment and/or ion exchange. The coal treatment is mainly used for removing discolorations and the ion exchanger is mainly used for removing formates and other impurities such as pentaerythritol monoformal.

To separate off the pure crystals of monopentaerythritol a band filter can appropriately be used at an industrial scale but a centrifuge is a possible alternative.

The obtained crystals of monopentaerythritol of high purity are suitably dried as a final process step. Monopentaerythritol of high purity is according to the invention defined as monopentaerythritol which has a purity of >99% by weight, preferably 99.3-99.9% by weight.

According to one embodiment of the invention the molar ratio of formaldehyde:acetaldehyde is approximately 5-7:1 and the monopentaerythritol of high purity is crystallized at a temperature of about 55-90° C. If the molar ratio of formaldehyde:acetaldehyde thereby is 6:1 the monopentaerythritol of high purity is appropriately crystallized at a temperature of about 60-80° C.

According to another embodiment of the invention the molar ratio of formaldehyde:acetaldehyde is approximately 7-9:1 and the monopentaerythritol of high purity is crystallized at a temperature of about 40-70° C. If the molar ratio of formaldehyde:acetaldehyde thereby is 9:1 the monopentaerythritol of high purity is appropriately crystallized at a temperature of about 45-60° C.

The pressure at evaporation suitably exceeds atmospheric pressure and the evaporated reaction mixture is cooled to a temperature of about 25-50° C., preferably about 30-40° C., to extract crystals of pentaerythritol.

The invention is explained in more detail in connection with the embodiment examples 1-8 below, of which examples 1-2 show a molar ratio between formaldehyde and acetaldehyde of 5.0:1.0, examples 3-5 show a molar ratio between formaldehyde and acetaldehyde of 6.0:1.0 and examples 6-8 show a molar ratio between formaldehyde and acetaldehyde of 9.0:1.0

EXAMPLE 1

Pentaerythritol was produced by a reaction between formaldehyde and acetaldehyde at a molar ratio of 5.0:1.0. Then, 3.08 parts by weight of acetaldehyde were added to an aqueous solution containing 10.51 parts by weight of formaldehyde and 7.47 parts by weight of an aqueous solution containing 45% sodium hydroxide. The molar ratio of water:acetaldehyde was 66:1. The reaction was exothermic and the temperature was permitted to rise to 50° C. The reaction mixture was neutralized with formic acid to a pH of 5.7. The pentaerythritol yield was about 90% calculated on acetaldehyde, which corresponds to 8.58 parts by weight of pentaerythritol.

The reaction mixture was evaporated to a dryness of 62% by weight and thereafter cooled to 35° C. Crystals of pentaerythritol thereby formed were separated off. The remaining process solution was treated separately to extract additional pentaerythritol and sodium formate.

The pentaerythritol crystals were dissolved into a clear and warm solution in a water-based mother liquor containing pentaerythritol, to a dryness of 45% by weight. The solution was purified through active coal treatment and a subsequent ion exchanger. Thereafter the solution was cooled to 84° C. and crystals of monopentaerythritol were precipitated. The crystals were separated off and 2.15 parts by weight of monopentaerythritol with a purity of 99.5% were obtained after drying. This corresponds to 25% of the total amount of pentaerythritol obtained. The purity was measured by gas chromatography.

The remaining amount of pentaerythritol, constituting 6.43 parts by weight, was processed into technical pentaerythritol.

EXAMPLE 2

The process according to example 1 was repeated with the difference that the crystals of pentaerythritol were dissolved into a clear and warm solution in a water-based mother liquor containing pentaerythritol, to a dryness of 55% by weight, and that the solution after the purification step was cooled to 90° C. Thereby pure monopentaerythritol was obtained in an amount corresponding to 40% of the total amount of pentaerythritol obtained.

EXAMPLE 3

Pentaerythritol was produced by a reaction between formaldehyde and acetaldehyde at a molar ratio of 6.0:1.0. Then, 3.08 parts by weight of acetaldehyde were added to an aqueous solution containing 12.61 parts by weight of formaldehyde and 7.47 parts by weight of an aqueous solution containing 45% sodium hydroxide. The molar ratio of water: acetaldehyde was 64:1. The reaction was exothermic and the temperature was permitted to rise to 50° C. The reaction mixture was neutralized with formic acid to a pH of 5.7. The pentaerythritol yield was about 92% calculated on acetaldehyde, which corresponds to 8.76 parts by weight of pentaerythritol.

The reaction mixture was evaporated to a dryness of 62% by weight and thereafter cooled to 35° C. Crystals of pentaerythritol thereby formed were separated off. The remaining process solution was treated separately to extract additional pentaerythritol and sodium formate.

The pentaerythritol crystals were dissolved into a clear and warm solution in a water-based mother liquor containing pentaerythritol, to a dryness of 45% by weight. The solution was purified through active coal treatment and a subsequent ion exchanger. Thereafter the solution was cooled to 70° C. and crystals of monopentaerythritol were precipitated and 5.43 parts by weight of monopentaerythritol with a purity of 99.6% were obtained after drying. This corresponds to 62% of the total amount of pentaerythritol obtained.

The remaining amount of pentaerythritol, constituting 3.43 parts by weight, was processed into technical pentaerythritol.

EXAMPLE 4

The process according to example 3 was repeated with the difference that the crystals of pentaerythritol were dissolved into a clear and warm solution in a water-based mother liquor containing pentaerythritol, to a dryness of 55% by weight, and that the solution after the purification step was cooled to 78° C. Thereby pure monopentaerythritol was obtained in an amount corresponding to 66% of the total amount of pentaerythritol obtained.

EXAMPLE 5

The process according to example 3 was repeated with the difference that the crystals of pentaerythritol were dissolved into a clear and warm solution in a water-based mother liquor containing pentaerythritol, to a dryness of 35% by weight, and that the solution after the purification step was cooled to 62° C. Thereby pure monopentaerythritol was obtained in an amount corresponding to 55% of the total amount of pentaerythritol obtained.

EXAMPLE 6

Pentaerythritol was produced by a reaction between formaldehyde and acetaldehyde at a molar ratio of 9.0:1.0. Then, 3.08 parts by weight of acetaldehyde were added to an aqueous solution containing 18.92 parts by weight of formaldehyde and 7.47 parts by weight of an aqueous solution containing 45% sodium hydroxide. The molar ratio of water: acetaldehyde was 59:1. The reaction was exothermic and the temperature was permitted to rise to 50° C. The reaction mixture was neutralized with formic acid to a pH of 5.7. The pentaerythritol yield was about 93% calculated on acetaldehyde, which corresponds to 8.86 parts by weight of pentaerythritol.

The reaction mixture was evaporated to a dryness of 62% by weight and thereafter cooled to 35° C. Crystals of pentaerythritol thereby formed were separated off. The remaining process solution was treated separately to extract additional pentaerythritol and sodium formate.

The pentaerythritol crystals were dissolved into a clear and warm solution in a water-based mother liquor containing pentaerythritol, to a dryness of 45% by weight. The solution was purified through active coal treatment and a subsequent ion exchanger. Thereafter the solution was cooled to 54° C. and crystals of monopentaerythritol were precipitated and 7.44 parts by weight of monopentaerythritol with a purity of 99.7% were obtained after drying. This corresponds to 84% of the total amount of pentaerythritol obtained.

The remaining amount of pentaerythritol, constituting 1.42 parts by weight, was processed into technical pentaerythritol.

EXAMPLE 7

The process according to example 6 was repeated with the difference that the crystals of pentaerythritol were dissolved into a clear and warm solution in a water-based mother liquor containing pentaerythritol, to a dryness of 35% by weight, and that the solution after the purification step was cooled to 46° C. Thereby pure monopentaerythritol was obtained in an amount corresponding to 80% of the total amount of pentaerythritol obtained.

EXAMPLE 8

The process according to example 6 was repeated with the difference that the crystals of pentaerythritol were dissolved into a clear and warm solution in a water-based mother liquor containing pentaerythritol, to a dryness of 55% by weight, and that the solution after the purification step was cooled to 60° C. Thereby pure monopentaerythritol was obtained in an amount corresponding to 86% of the total amount of pentaerythritol obtained.

The crystallization temperature depends on the dryness at the dissolving but also on the molar ratio between formaldehyde and acetaldehyde since the molar ratio determines the composition of the pentaerythritol that is dissolved. Generally the crystallization temperature is highest at the lowest molar ratio and for each molar ratio the crystallization temperature is highest at the highest dryness. At each molar ratio the crystallization temperature and the dryness can be combined to obtain monopentaerythritol of high purity.

The invention claimed is:
1. A process for production of a monopentaerythritol of high purity, said process comprising subjecting formaldehyde to reaction with acetaldehyde in an aqueous medium at a formaldehyde to acetaldehyde molar ratio of 5-10 to 1 and in the presence of a strong basic hydroxide and subsequently neutralizing the obtained reaction mixture, wherein said obtained reaction mixture is evaporated yielding a dryness of 50-70% by weight and is subsequently cooled, whereby formed pentaerythritol crystals are separated and recovered and subsequently dissolved in an aqueous mother liquor comprising pentaerythritol having a dryness of 35-55% by weight, said solution being treated in a purification step yielding monopentaerythritol of high purity crystallized at a temperature of 40-90° C., the obtained monopentaerythritol crystals being separated and recovered from remaining method liquor and said remaining mother liquor being re-circulated to said purification step.

2. The process according to claim 1, wherein said strong basic hydroxide is an alkali metal hydroxide or an alkaline earth metal hydroxide.

3. The process according to claim 2, wherein said alkali metal hydroxide is sodium hydroxide.

4. The process according to claim 1, wherein said formaldehyde to acetaldehyde molar ratio is 7-9 to 1.

5. The process according to claim 1, wherein an evaporation pressure exceeding atmospheric pressure is used.

6. The process according to claim 1, wherein the obtained evaporated reaction mixture is cooled to a temperature of 25-50° C., to extract crystals of pentaerythritol.

7. The process according to claim 1, wherein the obtained evaporated reaction mixture is cooled to a temperature of 30-40° C., to extract crystals of pentaerythritol.

8. The process according to claim 1, wherein said monopentaerythritol of high purity is crystallized at a temperature of 60-80° C.

9. The process according to claim 1, wherein said purification step comprises a coal treatment and/or an ion exchange.

10. The process according to claim 1, wherein a band filter or a centrifuge is used for separation and recovery.

11. The process according to claim 1, wherein the obtained crystals of monopentaerythritol are dried.

12. The process according to claim 1, wherein the obtained monopentaerythritol has a purity of >99% by weight.

* * * * *